United States Patent [19]
DeJournett

[11] Patent Number: 4,922,929
[45] Date of Patent: May 8, 1990

[54] PADDED ELBOW BRACE

[76] Inventor: Richard L. DeJournett, 1804 Alaweo St., Honolulu, Hi. 96821

[21] Appl. No.: 401,190

[22] Filed: Aug. 31, 1989

[51] Int. Cl.[5] .................. A61F 13/00; A41D 13/08
[52] U.S. Cl. ............................................. 128/892; 2/16
[58] Field of Search .............. 128/892, 878, 881, 882, 128/77, 879, 165; 2/16, 22, 24, 161 A

[56] References Cited

U.S. PATENT DOCUMENTS

| | | | |
|---|---|---|---|
| Re. 32,680 | 5/1988 | Pompa | 128/881 |
| 1,113,020 | 10/1914 | King | 2/16 |
| 1,846,835 | 2/1932 | Bruckler | 2/16 |
| 2,211,203 | 8/1940 | Goldman | 128/881 |
| 2,626,394 | 1/1953 | Davis | 2/24 |
| 3,266,058 | 8/1966 | Guttman | 2/16 |
| 3,322,118 | 5/1967 | Sotherlin | 128/892 |
| 3,504,379 | 4/1970 | Glick | 2/161 A |
| 3,648,291 | 3/1972 | Pankers | 128/892 |
| 3,945,046 | 3/1976 | Stromgren | 2/22 |
| 3,990,440 | 11/1976 | Gaylord, Jr. | 128/892 |
| 4,120,052 | 10/1978 | Butler | 2/16 |
| 4,150,442 | 4/1979 | Boone | 128/892 |
| 4,292,263 | 9/1981 | Hanrahan et al. | 264/469.9 |
| 4,315,504 | 2/1982 | Drennan et al. | 128/892 |
| 4,484,361 | 11/1984 | Leighton | 2/16 |

Primary Examiner—Robert A. Hafer
Assistant Examiner—Michael Brown
Attorney, Agent, or Firm—Shlesinger & Myers

[57] ABSTRACT

A device for protecting limb joints which is generally in the form of a tubular member that can be easily slipped onto a limb joint. The tubular member includes upper and lower sections connected to each other so as to form an open ended cavity therebetween. The lower section is generally hourglass shaped and is made of a stretchable elastic material. The upper section includes crossover pieces and is also made of a stretchable elastic material. A protective cushion corresponding in size to the lower section is disposed in the cavity. Only the ends of the cushion are stitched to the lower section so as to create a pocket between the cushion and the lower section. A resilient reinforcing pad is removably secured in the pocket.

11 Claims, 3 Drawing Sheets

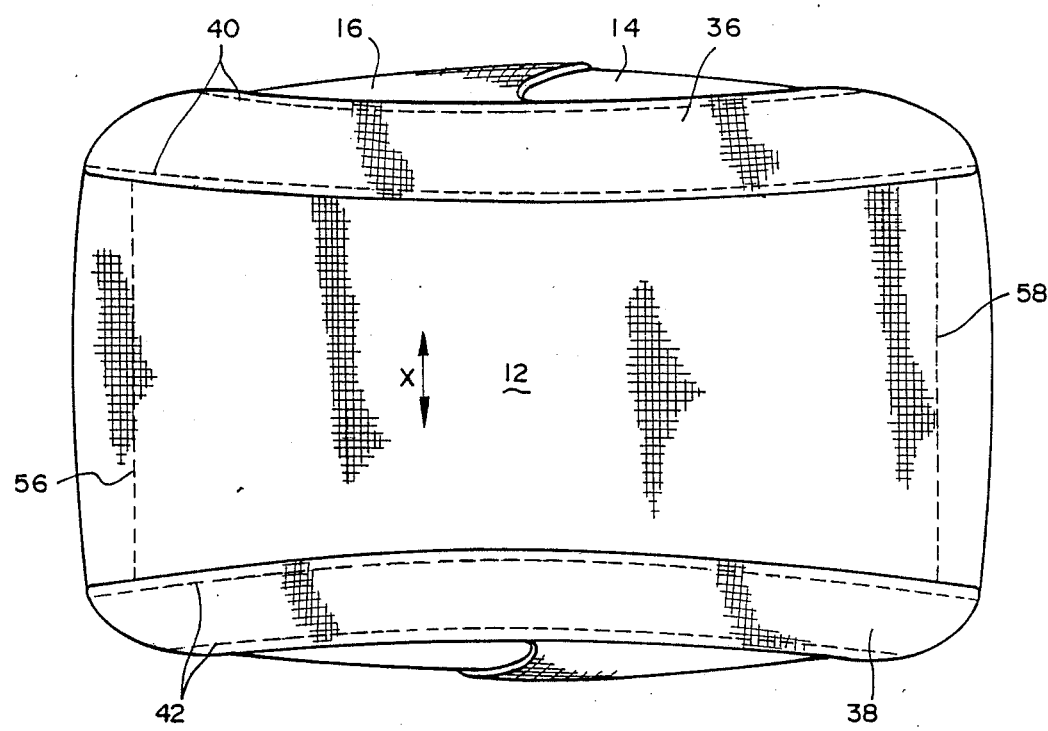
FIG_3
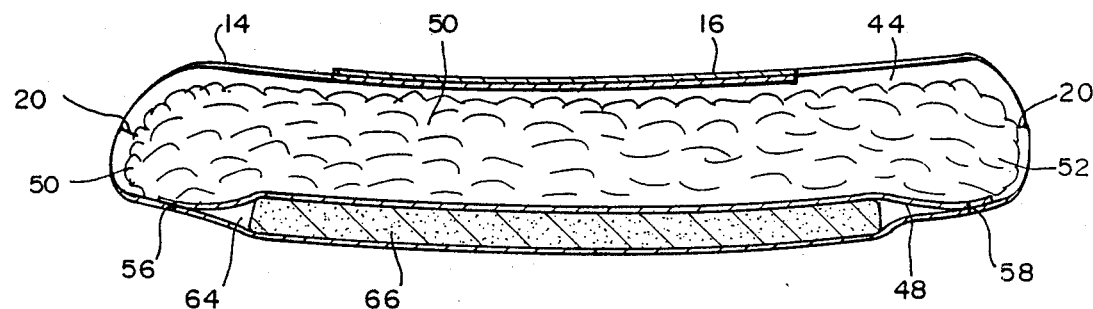
FIG_4
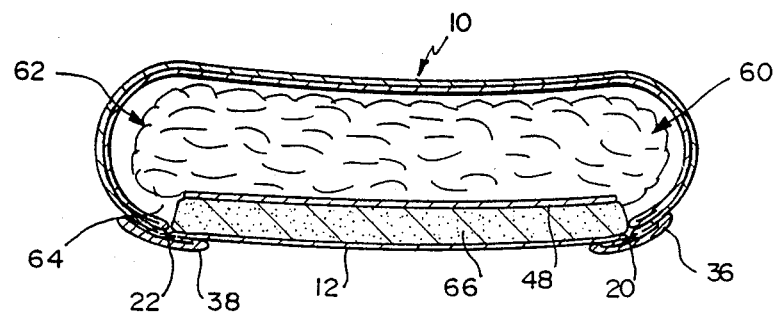
FIG_5

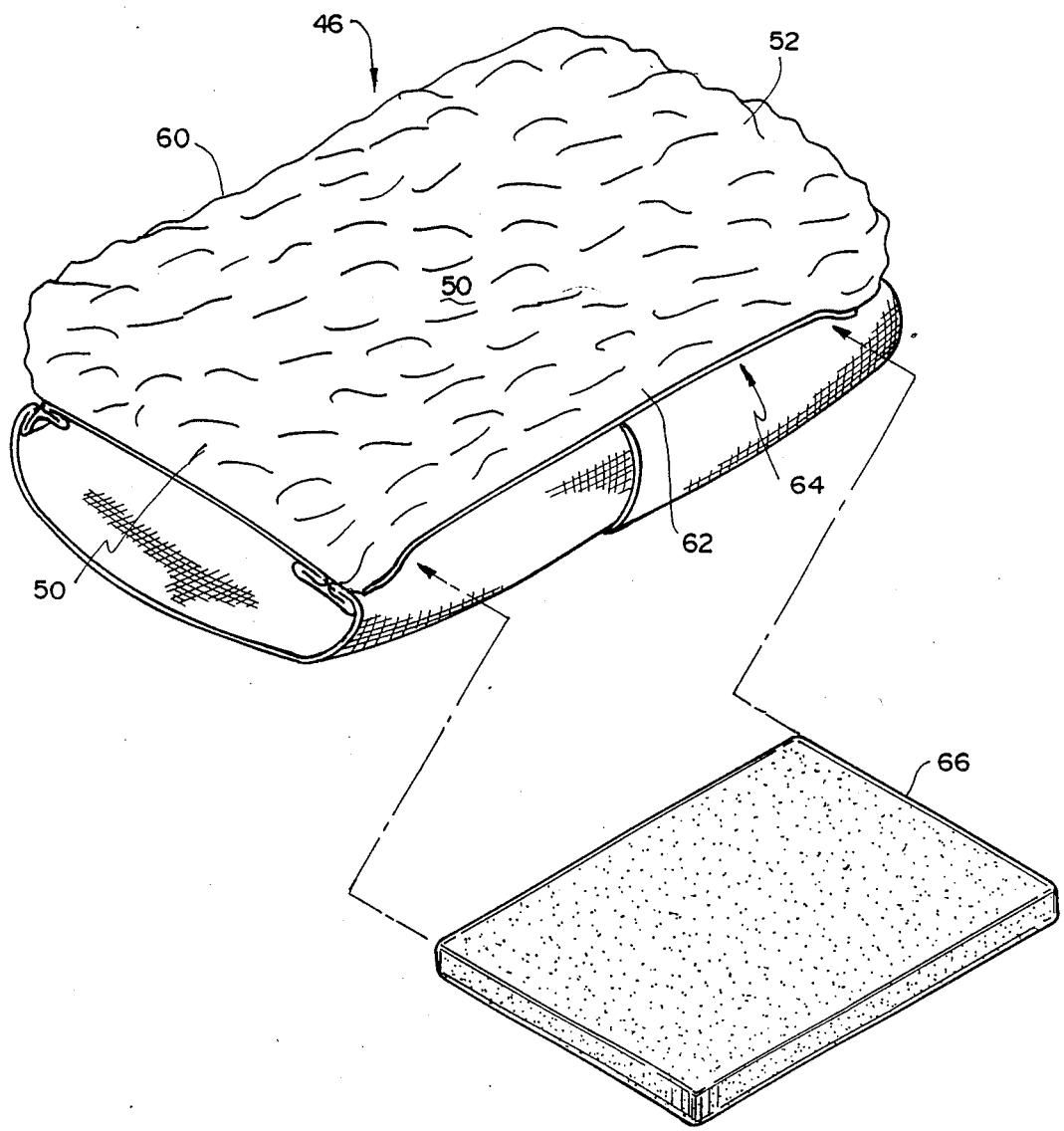
FIG_6

PADDED ELBOW BRACE

FIELD AND HISTORICAL BACKGROUND OF THE INVENTION

The present invention is generally directed to devices for protecting limb joints, and more particularly to a padded elbow brace.

In the health care field, particularly in the hospitals and the like, patients who are bed-ridden or otherwise confined, develope sores by contact, as in rubbing with various other objects during the treatment or in the confinement phase of the treatment. Most often, these sores occur on the limb joints, such as the elbows, knees, and the heels. These sores most often develop from rubbing or abrasive action with various surrounding objects, such as bedframes, handrests on a wheelchair, or the hard table top surface of a radiographic machine. Therefore, it often becomes difficult to render treatment or to conduct various routine examinations on a patient. This is particularly true in the situation where, for example, a patient had sustained an injury in or in the area of a limb joint, and it becomes necessary to conduct an x-ray examination. Various methods and devices have been developed for safeguarding patients against such sores or preventing from further exaggeration of an existing injury, but none of them has been found to be entirely satisfactory. Examples of various conventional devices and methods are disclosed in U.S. Pat. Nos. 1,113,020; 2,626,394; 3,322,118; 3,504,379; 3,945,046; 4,150,442; 4,292,263; 4,315,504; and Re 32,680.

OBJECTS AND SUMMARY OF THE INVENTION

The principal object of the present invention is to provide a device for protecting limb joints which prevents a patient from sustaining any injury or developing sores on and around a joint.

Another object of the present invention is to provide a device for protecting limb joints which prevents any further exaggeration of existing sores or an injury on or around the joint of a patient.

Yet another object of the present invention is to provide a device for protecting limb joints which greatly facilitates radiographic examination of the limb joint of a patient by a physician.

Yet another object of the present invention is to provide a device for protecting limb joints from abrasion and injury during rotation and movement of the patient undergoing various X-ray procedures.

Still yet another object of the present invention is to provide a device for protecting limb joints which can be easily slipped over a limb joint easily, comfortably and without any pain to the patient.

An additional object of the present invention is to provide a device for protecting limb joints which is easy to handle and relatively inexpensive to manufacture.

Yet an additional object of the present invention is to provide a device for protecting limb joints which is very pliable, facilitating comfortable fitting over the limb joint of a patient and adapting to various movements of the limb.

A further object of the present invention is to provide a device for protecting limb joints which is simple in design and construction thereby easy to make in different sizes, for adults and for the children, and for various limb joints of a patient.

Yet an additional object of the present invention is to provide a device for protecting limb joints which requires minimal handling and care by a patient, and can be easily washed in household clothes washing machines and subsequently dried in household clothes dryers.

In summary, the main object of the present invention is to provide a device for protecting limb joints which can be easily applied to and removed from a patient's limb joint during medical treatment, and particularly during a radiographic examination.

BRIEF DESCRIPTION OF THE DRAWINGS

The above and other objects and advantages and novel features of the present invention will become apparent from the following detailed description of the preferred embodiment of the invention illustrated in the accompanying drawings, wherein:

FIG. 3 is a bottom plan view of the device shown in FIG. 2;

FIG. 4 is a view taken along line 4—4 of FIG. 2;

FIG. 5 is a view taken along line 5—5 of FIG. 2; and

FIG. 6 is a view of the device inverted outwardly.

DETAILED DESCRIPTION OF THE INVENTION

Figure 1:
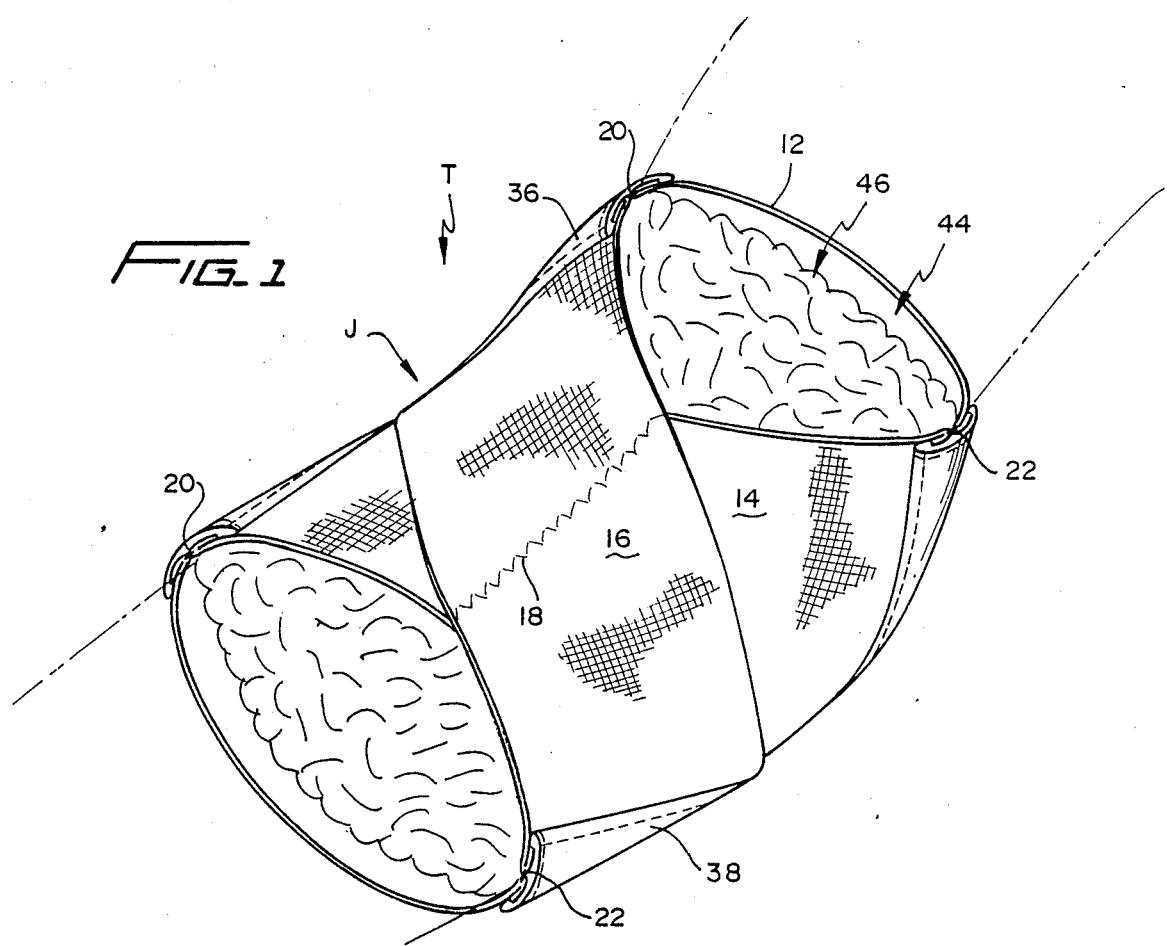
FIG. 1 illustrates the limb joint protecting device of the invention fitted over the elbow of a patient shown in phantom lines.
Figure 2:
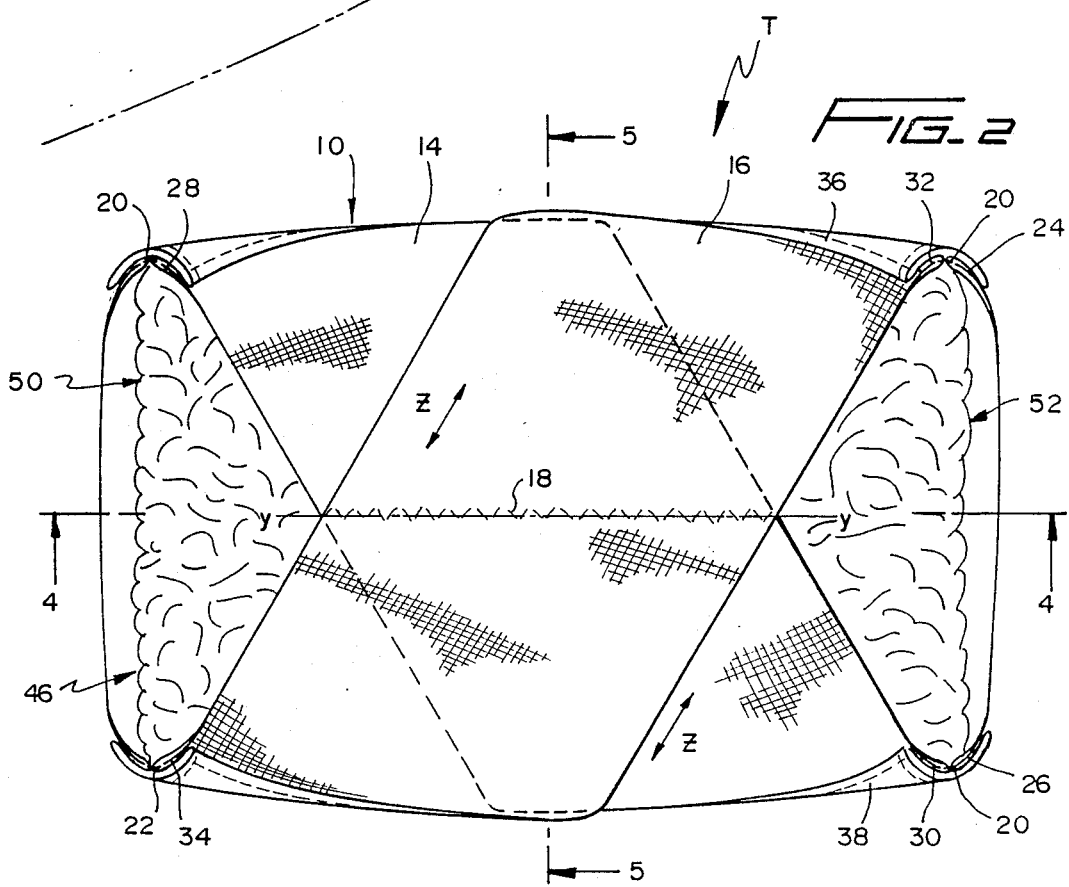
FIG. 2 is a top plan view of the device of the present invention.

As shown in FIGS. 1–3, the limb joint protecting device of the present invention is in the form of a generally rectangular tubular member T that can be easily slipped onto a limb joint J of the patient (FIG. 1). The tubular member T is composed of upper section 10 (FIG. 2) and lower section 12 (FIG. 3). The entire tubular member T may be made from a conventional stretchable elastic material. As shown in FIG. 3, lower section 12 is generally hourglass-shaped and is stretchable only transverse direction, shown by arrow X. The upper section 10 is composed of two crossover pieces 14 and 16 which are sewn together with a single row of widely spaced zigzag stitching 18 running generally along a longitudinal axis Y of tubular member T. The crossover pieces 14 and 16 are generally stretchable in the direction in which they extend, shown by arrows Z in FIG. 2. The tubular member is generally laterally symmetrical about a vertical plane extending through longitudinal axis Y thereof.

The upper and lower sections 10 and 12 are stitched together at left and right side seams 20 and 22. As best shown in FIGS. 1 and 2, side end portions 24 and 26 of lower section 12, and side end portions 28, 30 of crossover piece 14 and side end portions 32, 34 of crossover piece 16, are folded outwardly such that side seams 20 and 22 lie towards the exterior of tubular member T so as not to chafe or tear the patient's skin. Side braces 36 and 38 made of a suitable cloth or the like material are stitched over side means 20 and 22, respectively. In FIG. 3, reference numerals 40 and 42 designate side seams for stitching side braces 36 and 38. It should be noted that additional stitchings may be provided, if needed.

As shown in FIGS. 1 and 4 the upper and lower sections 10 and 12 define therebetween an open ended cavity 44. A protective cushion 46 generally corresponding in size to lower section 12 is disposed within cavity 44 (FIG. 4). The cushion 46 is preferably made of a natural lambskin. As used herein, the cushion material is being referred to generically as hide, which is constituted by the outer covering of the animal and includes skin 48 and wool 50 thereon (FIG. 4).

The protective cushion 46 substantially conforms to and occupies cavity 44 and is connected to lower section 12 adjacent its ends 52 and 54 by stitching at seams 56 and 58 (FIGS. 3 and 4). In other words, cushion 46 is sewn to lower section 12 only at its ends 52 and 54, and its sides 60 and 62 remain free. As shown in FIG. 5, a pocket 64 is thereby created between cushion 46 and lower section 12. A reinforcement pad 66 made of a resilient material is placed in pocket 64 as shown in FIGS. 4-6. The pad 66 conforms to pocket 64 and can be easily slipped in or taken out therefrom as it is not sewn or stitched to any part of tubular member T. Preferably, pad 66 is made from a foam or the like material and has a minimum thickness of about 1 cm and its density is sufficient so as to provide adequate reinforcement for protective cushion 46. Preferably, the dimensions of cushion 46 and pad 66 correspond to the dimensions of lower section 12.

The width of each crossover piece 14 and 16 is slightly larger than one-half the length of lower section 12 to provide for sufficient overlapping of crossover pieces 14 and 16. This arrangement further prevents the lose skin of a patient from being entrapped between crossover pieces 14 and 16.

As noted above, lower section 12 is only stretchable in transverse direction indicated by arrow X in FIG. 3. This construction allows for conformation with the underlying pad 66, i.e., a stretch in the longitudinal direction, indicated by axis Y in FIG. 2, is not possible as non-stretchable cushion 46 is sewn to lower section 12 at seams 56 and 58 (FIG. 4).

As would be apparent to those of ordinary skill in the art, the tubular member T may be made in different sizes and shapes, for adults and for children, and to accommodate different limb joints.

While this invention has been described as having a preferred design, it is understood that it is capable of further modifications uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

What is claimed is:

1. A device for protecting limb joints, comprising:
   (a) a generally tubular member to be slipped onto a limb joint;
   (b) said tubular member including first and second sections connected to each other so as to form an open ended cavity therebetween;
   (c) said first section being generally hourglass shaped and made of a stretchable material;
   (d) said second section including crossover pieces;
   (e) cushion means corresponding in size to said first section and disposed within said cavity;
   (f) said cushion means including first and second ends and sides;
   (g) said cushion means is connected to said first section at said first and said second ends are unconnected on said sides thereof thereby creating a pocket between said cushion means and said first section;
   (h) said pocket being open on said sides and closed at said first and second ends; and
   (i) resilient pad means removably positioned within said pocket and generally conforming to said pocket whereby said resilient pad means may be slipped in and out of said pocket.
2. The device of claim 1, wherein;
   (a) said first and second sections are stitched to each other in a manner that the seam lies towards the exterior of said tubular member.
3. The device of claim 2, and including;
   (a) a side brace generally covering the seam and substantially extending the length of said tubular member.
4. The device of claim 1, wherein:
   (a) said crossover pieces are made of a stretchable material.
5. The device of claim 1, wherein:
   (a) said crossover pieces are sewn to each other by a row of zigzag stitching.
6. The device of claim 1, wherein:
   (a) said first section is stretchable only in a transverse direction.
7. The device of claim 1, wherein:
   (a) the width of each of said crossover pieces exceeds one-half the length of said first section.
8. The device of claim 1, wherein:
   (a) said cushion means is formed of a natural hide including a leather layer and wool layer; and
   (b) said wool layer substantially fills up said cavity.
9. The device of claim 8, wherein:
   (a) said hide is natural lambskin.
10. The device of claim 1, wherein:
    (a) said pad means is made of a foam material.
11. The device of claim 10, wherein:
    (a) said pad means has a thickness of about 1.0 cm.

* * * * *